United States Patent
Kohara et al.

(10) Patent No.: US 10,070,841 B2
(45) Date of Patent: Sep. 11, 2018

(54) ARITHMETIC DEVICE, X-RAY CT APPARATUS, AND IMAGE RECONSTRUCTION METHOD

(71) Applicant: HITACHI, LTD., Tokyo (JP)

(72) Inventors: Ryota Kohara, Tokyo (JP); Tsuyoshi Suzuki, Tokyo (JP); Yuta Ogura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/542,688

(22) PCT Filed: Feb. 2, 2016

(86) PCT No.: PCT/JP2016/052972
§ 371 (c)(1),
(2) Date: Jul. 11, 2017

(87) PCT Pub. No.: WO2016/132880
PCT Pub. Date: Aug. 25, 2016

(65) Prior Publication Data
US 2017/0347986 A1     Dec. 7, 2017

(30) Foreign Application Priority Data
Feb. 16, 2015 (JP) .................. 2015-027399

(51) Int. Cl.
*A61B 6/00*      (2006.01)
*G06T 11/00*    (2006.01)
*A61B 6/03*     (2006.01)

(52) U.S. Cl.
CPC ............ *A61B 6/5258* (2013.01); *A61B 6/032* (2013.01); *A61B 6/5205* (2013.01);
(Continued)

(58) Field of Classification Search
CPC ........ A61B 6/032; A61B 6/466; A61B 6/5205; A61B 6/5235; A61B 6/5258;
(Continued)

(56) References Cited

U.S. PATENT DOCUMENTS 6,507,633 B1 *   1/2003   Elbakri .............. G06T 11/006
                                                       378/4
8,917,922 B2    12/2014   Zamyatin et al.
(Continued)

FOREIGN PATENT DOCUMENTS

JP         2014-407       1/2014
WO    WO2013/008702 A1    1/2013

OTHER PUBLICATIONS

Erdogan et al. "Ordered subsets algorithms for transmission tomography." Physics in Medicine & Biology 44.11 (1999): 2835.*
(Continued)

*Primary Examiner* — Katrina Fujita
(74) *Attorney, Agent, or Firm* — Cooper & Dunham LLP

(57) ABSTRACT

In order to provide an arithmetic device, an X-ray CT apparatus, and an image reconstruction method, capable of reducing processing time while maintaining a noise reduction effect, in a successive approximation image reconstruction method (separable paraboloidal surrogate (SPS) method) of the related art, updated images are forward-projected, whenever images are repeatedly updated, a difference between forward projection data and original object projection data is back-projected so that a difference image is obtained, and a forward projection process and a back projection process are repeatedly performed, but, in the present invention, a forward projection process and a back projection process requiring calculation time are replaced with a process requiring a relatively small calculation amount, such as a difference between an updated image and a reference image, and, as a result, it is possible to consid-
(Continued)

erably reduce a calculation amount in a successive approximation image reconstruction process and to reduce processing time.

12 Claims, 13 Drawing Sheets

(52) U.S. Cl.
CPC .......... *A61B 6/5235* (2013.01); *G06T 11/006* (2013.01); *G06T 11/008* (2013.01); *A61B 6/466* (2013.01); *G06T 2210/41* (2013.01); *G06T 2211/404* (2013.01); *G06T 2211/421* (2013.01)

(58) Field of Classification Search
CPC . G06T 11/006; G06T 11/008; G06T 2210/41; G06T 2211/404; G06T 2211/421
See application file for complete search history.

(56) References Cited

U.S. PATENT DOCUMENTS

| | | | | |
|---|---|---|---|---|
| 9,123,098 | B2* | 9/2015 | Takahashi | A61B 6/032 |
| 9,595,121 | B2* | 3/2017 | Ahn | G06T 11/006 |
| 2010/0080430 | A1* | 4/2010 | Souza | G06T 7/11 |
| | | | | 382/131 |
| 2010/0246917 | A1* | 9/2010 | Bruder | A61B 6/032 |
| | | | | 382/131 |
| 2012/0039518 | A1* | 2/2012 | Bruder | A61B 6/032 |
| | | | | 382/131 |
| 2012/0057770 | A1* | 3/2012 | Jang | G06T 11/005 |
| | | | | 382/132 |
| 2012/0128265 | A1* | 5/2012 | Silver | G06T 11/006 |
| | | | | 382/275 |
| 2012/0308104 | A1* | 12/2012 | Yang | G06T 5/002 |
| | | | | 382/131 |
| 2013/0188847 | A1* | 7/2013 | Zou | G06T 5/002 |
| | | | | 382/131 |
| 2014/0140601 | A1* | 5/2014 | Litvin | G06T 11/005 |
| | | | | 382/131 |
| 2014/0193055 | A1* | 7/2014 | Takahashi | G06T 11/006 |
| | | | | 382/131 |
| 2014/0334701 | A1* | 11/2014 | Ye | G06T 11/006 |
| | | | | 382/131 |
| 2014/0363067 | A1* | 12/2014 | Stayman | G06T 11/005 |
| | | | | 382/131 |
| 2015/0190106 | A1* | 7/2015 | Yamakawa | A61B 6/032 |
| | | | | 378/4 |
| 2015/0348289 | A1* | 12/2015 | Ida | A61B 6/032 |
| | | | | 382/131 |
| 2016/0110893 | A1* | 4/2016 | Pang | A61B 6/5205 |
| | | | | 382/131 |
| 2016/0143606 | A1* | 5/2016 | Yamakawa | A61B 6/032 |
| | | | | 378/19 |
| 2016/0151035 | A1* | 6/2016 | Noda | A61B 6/032 |
| | | | | 378/26 |
| 2017/0119335 | A1* | 5/2017 | Yamakawa | A61B 6/032 |
| 2017/0135659 | A1* | 5/2017 | Wang | G06T 11/005 |

OTHER PUBLICATIONS

Hu et al. "L0 constrained sparse reconstruction for multi-slice helical CT reconstruction." Physics in Medicine & Biology 56.4 (2011): 1173.*

Niu et al. "Sparse-view x-ray CT reconstruction via total generalized variation regularization." Physics in Medicine & Biology 59.12 (2014): 2997.*

International Search Report dated May 10, 2016 in connection with PCT/JP2016/052972.

* cited by examiner

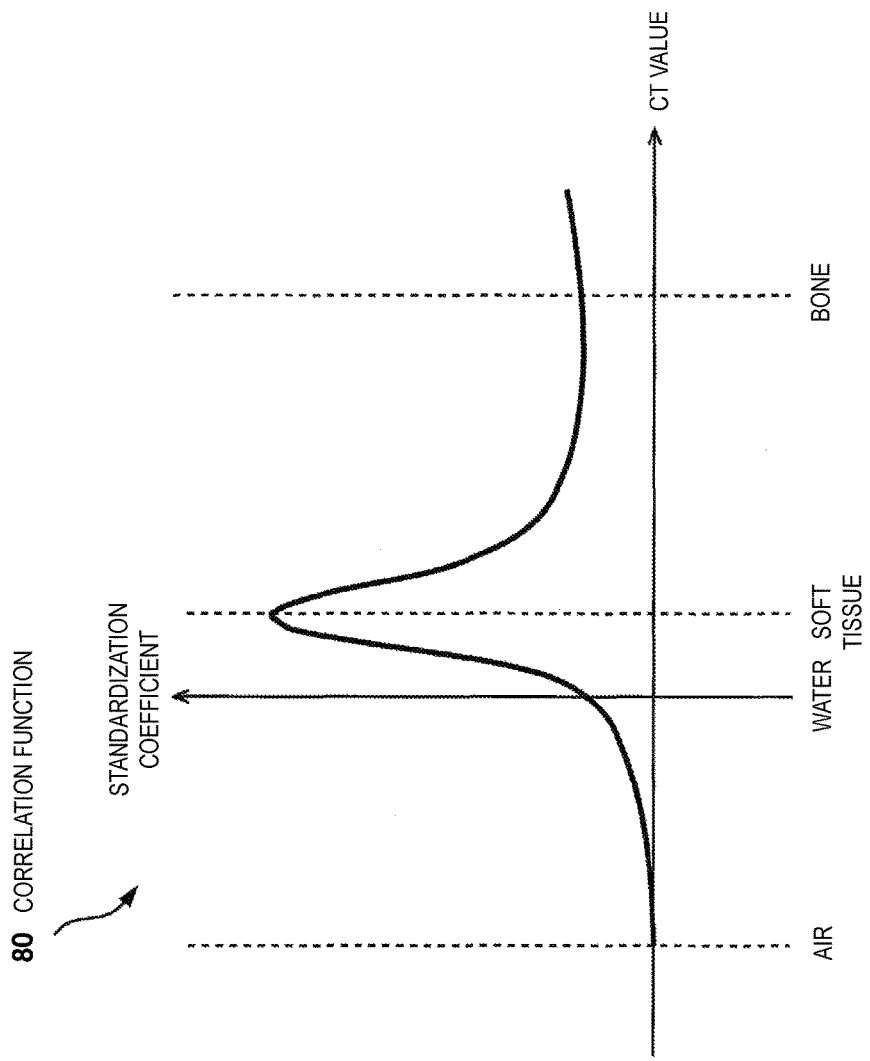

ARITHMETIC DEVICE, X-RAY CT APPARATUS, AND IMAGE RECONSTRUCTION METHOD

TECHNICAL FIELD

The present invention relates to an arithmetic device, an X-ray CT apparatus, and an image reconstruction method, and particularly to a fast noise reduction processing technique in image reconstruction according to a successive approximation reconstruction method.

BACKGROUND ART

In recent years, in order to perform CT examination in which, a radiation exposure dose is small, image reconstruction has been performed according to a successive approximation method in which an image with less noise even in a small dose can be obtained.

PTL 1 discloses an update formula used for a separable paraboloidal surrogate method (SPS method) which is one kind of the successive approximation method as expressed in Equation (1).

$$\mu_j^{(n+1)} = \mu_j^{(n)} - \frac{\sum \gamma_{ij}(y_i - \sum a_{ik}\mu_k^{(n)}) + \beta \sum w_{jk}\phi(\mu_j^{(n)} - \mu_k^{(n)})}{d_j + 2\beta \sum w_{jk}\omega_\psi(\mu_j^{(n)} - \mu_k^{(n)})} \quad (1)$$

In Equation (1), μ is an updated pixel value, y is an original projection value, β is a normalization, coefficient, d is a standardization coefficient, w is a pixel coefficient, i is a detected element number, j and k are pixel number, and n. is the number of times of repetition, In addition, γ is an element of a matrix for converting a projection value into a pixel value, a is an element of a matrix for converting a projection value into a pixel value, $\Sigma\gamma_{ij}$ indicates a back projection process, and $\Sigma a_{ij}$ indicates a forward projection process. A linear component of a substitute function Ψ of a potential function (also referred to as penalty term) is indicated by ϕ, and a quadratic component thereof is indicated by ω.

CITATION LIST

Patent Literature

PTL 1: International Publication Ho. 2013/008702

SUMMARY OF INVENTION

Technical Problem

However, the update formula shown as the above Equation (1) includes the back projection process $\Sigma\gamma_{ij}$ and forward projection process $\Sigma a_{ij}$ which are matrix calculation processes causing a large calculation load. Thus, there is a problem in that a calculation amount increases, and processing time also increases.

The present invention has been made in consideration of the above-described problem, and ail object thereof is to provide an arithmetic device, an X-ray CT apparatus, and an image reconstruction method, capable of reducing processing time while maintaining a noise reduction effect in a successive approximation image reconstruction method.

Solution to Problem

In order to achieve the above-described object, according to the present invention, there is provided an arithmetic device including a projection data creation unit that creates object projection data on the basis of information regarding X-rays which are irradiated from respective directions around an object and are transmitted through the object; a reference image creation unit that creates a reference image on the basis of the object projection data; a standardized image creation unit that creates a standardized image in which a standardization coefficient for adjusting the noise reduction intensity in an update process is defined for each pixel; and a repetitive processing unit that performs repetitive processes a predetermined number of times by using the reference image and the standardized image, in which the repetitive processing unit includes a difference image creation portion that obtains a difference between the reference image and an updated image which is obtained through the update process, so as to create a difference image, and an image update portion that performs the update process by using the difference image and the standardized image, so as to create an updated image.

According to the present invention, there is provided an X-ray CT apparatus including the arithmetic device.

There is provided an image reconstruction method including causing an arithmetic device to execute a projection data creation step of creating object projection data on the basis of information regarding X-rays which are irradiated from respective directions around an object and are transmitted through the object; a reference image creation step of creating a reference image on the basis of the object projection data; a standardized image creation step of creating a standardized image in which a standardization coefficient for adjusting the noise reduction intensity in an update process is defined for each pixel; and a repetitive processing step of performing repetitive processes a predetermined number of times by using the reference image and the standardized image, in which the repetitive processing step includes a difference image creation step of obtaining a difference between the reference image and an updated image which is obtained through the update process, so as to create a difference image, and an image update step of performing the update process by using the difference image and the standardized image, so as to create an updated image.

Advantageous Effects of Invention

According to the present invention, a forward projection process and a back projection process which are matrix calculation processes causing a large calculation load are omitted from an update formula, and are replaced with image processing causing a small calculation load, and thus it is possible to provide an arithmetic device, an X-ray CT apparatus, and an image reconstruction method, capable of reducing processing time while maintaining a noise reduction effect.

BRIEF DESCRIPTION OF DRAWINGS

FIG. 13 illustrates an example of a correlation function 80 indicating a correlation between a CT value and a standardization coefficient.

DESCRIPTION OF EMBODIMENTS

Hereinafter, a preferred embodiment of the present invention will be described in detail with reference to the drawings. First, with reference to FIGS. 1 and 2, a hardware configuration of an X-ray CT apparatus 1 will be described.

Figure 1:
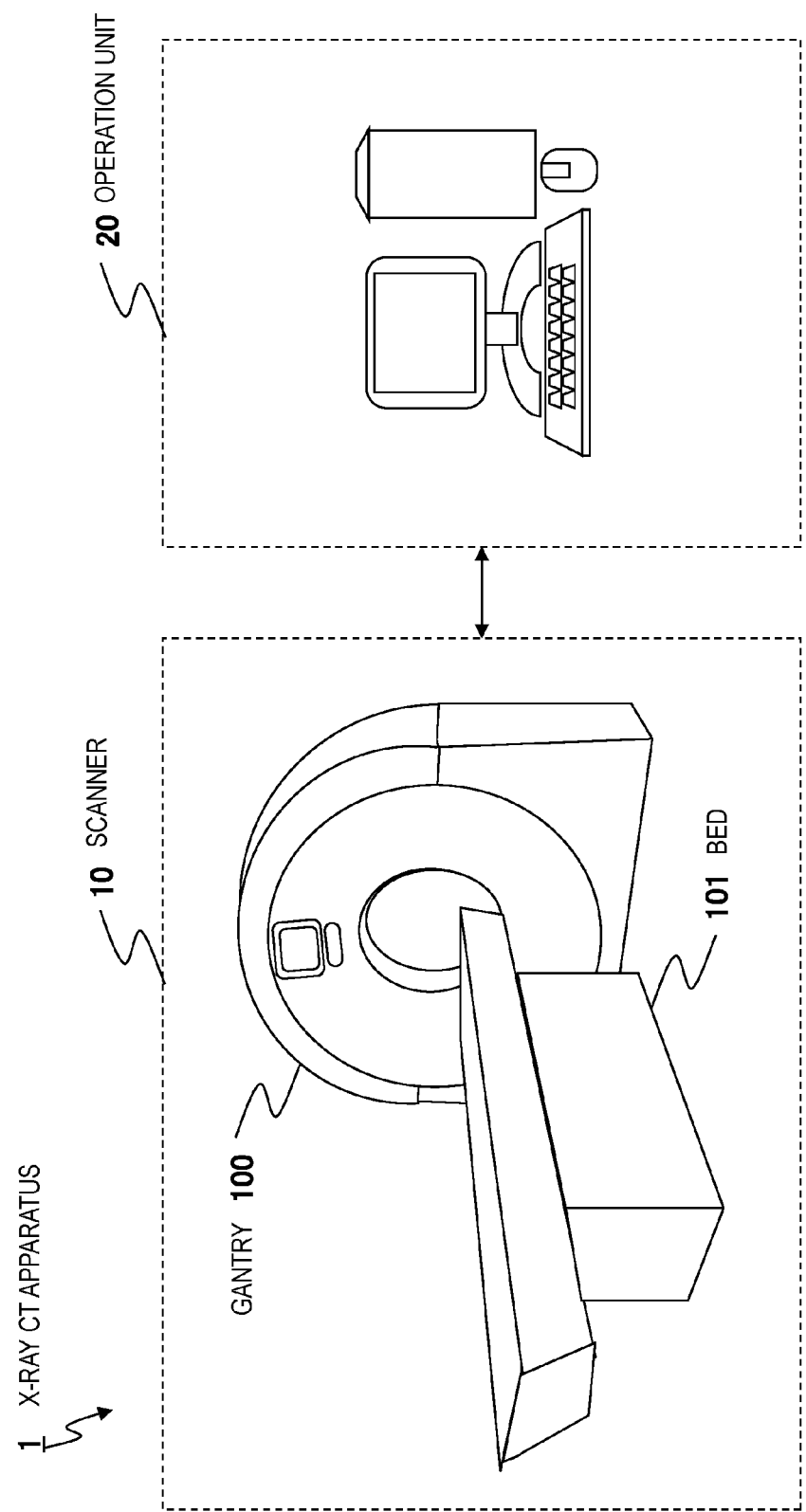
FIG. 1 is an exterior diagram illustrating the entire configuration of an X-ray CT apparatus 1.
Figure 2:
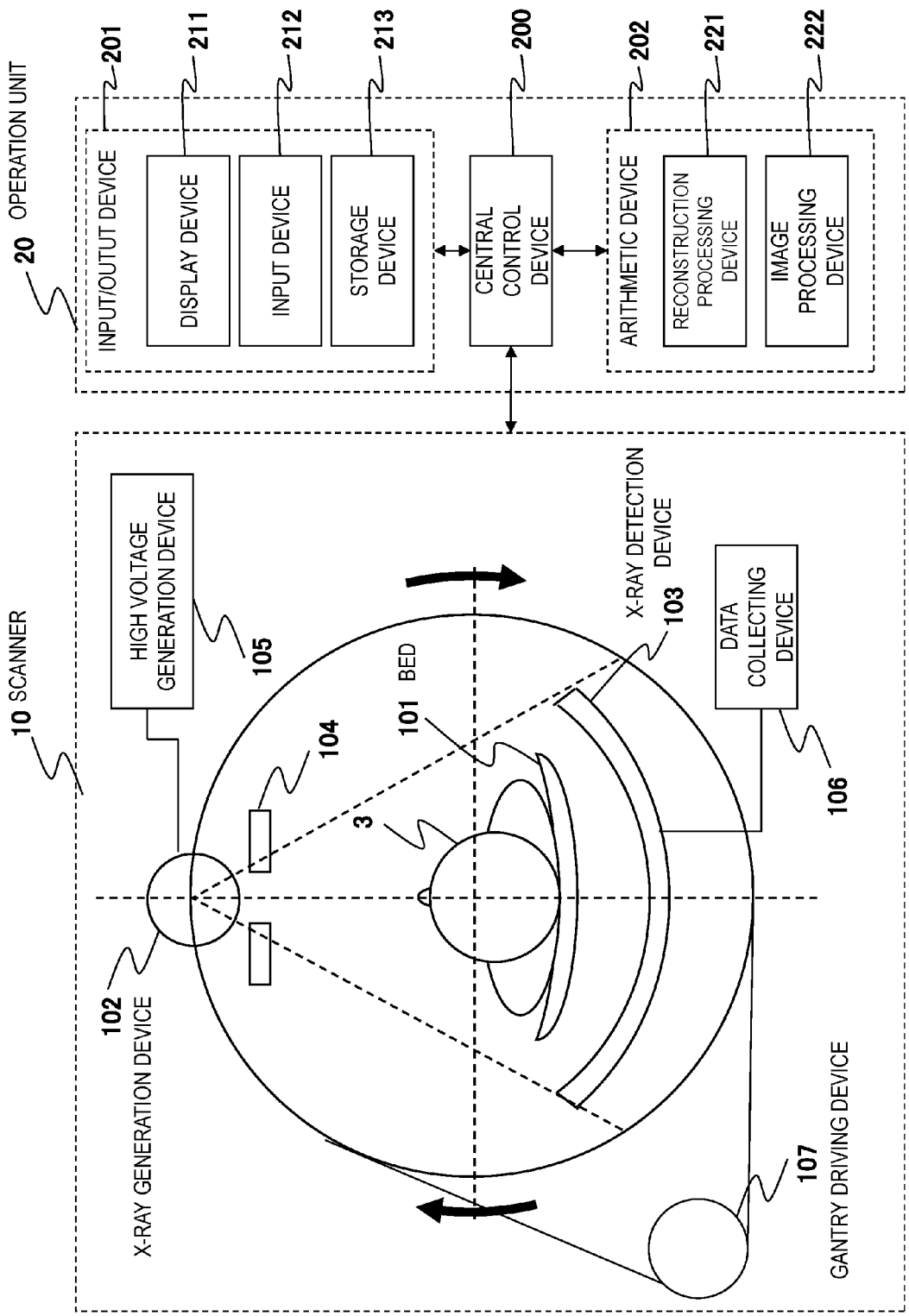
FIG. 2 is a block diagram illustrating an internal configuration of the X-ray CT apparatus 1.

As illustrated in FIGS. 1 and 2, the X-ray CT apparatus 1 is roughly formed of a scanner 10 and an operation unit 20. The scanner 10 includes a gantry 100 and a bed 101. The gantry 100 includes an X-ray generation device 102, an X-ray detection device 103, a collimator 104, a high voltage generation device 105, a data collecting device 106', a gantry driving device 107, and the like. The operation unit 20 includes a central control device 200, an input/output device 201, an arithmetic device 202, and the like.

An operator inputs scanning conditions, reconstruction conditions, or the like by using the input/output device 201 of the operation unit 20. The scanning conditions are, for example, an X-ray beam width, a bed movement speed, a tube current, a tube voltage, a scanning range (body axis direction range), and the number of scanning views per circumferential rotation. The reconstruction conditions are, for example, a region of interest, a field of view (FOV), and a reconstruction filter function. The input/output device 201 includes a display device 211 which displays a CT image or the like, an input, device 212 which includes a mouse, a track ball, a keyboard, a touch panel, and the like, a storage device 213 which stores data, and the like.

The central control device 200 is a computer including a central processing unit (CPU), a read only memory (ROM), a random access memory (RAM), and the like, and controls the entire operation of the X-ray CT apparatus 1. The central control device 200 transmits control signals required for scanning to the respective devices of the scanner 10 on the basis of the scanning conditions or the reconstruction conditions.

If scanning is started by receiving a scanning start signal from the central control device 200, the high voltage generation device 105 applies a tube voltage and a tube current with predetermined magnitudes to the X-ray generation device 102 on the basis of control signals from the central control device 200. The X-ray generation device 102 emits electrons with energy corresponding to the applied tube voltage from a cathode thereof, and irradiates an object 3 with X-rays with energy corresponding to the electron energy as a result of the emitted electrons colliding with a target (anode).

An irradiation region of the X-rays irradiated from the X-ray generation device 102 is restricted by the collimator 104. An aperture width of the collimator 104 is controlled on the basis of a control signal from the central control device 200.

The X-ray CT apparatus 1 is roughly classified into a multi-slice CT apparatus using the X-ray detection device 103 in which detection elements are arranged in a two-dimensional direction, and a single-slice CT apparatus using the X-ray detection device 103 in which detection elements are arranged in one column, that is, a one-dimensional direction (only a channel direction). In the multi-slice CT apparatus, an X-ray beam which spreads in a conical shape or a pyramidal shape is irradiated from the X-ray generation device 102 which is an X-ray source in accordance with the X-ray detection device 103. In the single-slice. CT apparatus, an X-ray beam which spreads in a fan-like shape is irradiated from the X-ray generation device 102.

The X-rays whose irradiation region is restricted by the collimator 104 after being irradiated from the X-ray generation device 102 are absorbed (attenuated) in each tissue of the object 3 according to an X-ray attenuation coefficient, and then pass through the object 3, so as to be detected by the X-ray detection device 103 disposed at a position opposing the X-ray generation device 102.

The bed 101 includes a top plate on which the object 3 is mounted and laid, a lifting driving device, and a top plate driving device, and vertically moves up and down the top plate, moves the top plate in a front-and-rear direction along a body axis direction, or moves the top plate in a direction (leftward-and-rightward direction) which is perpendicular to the body axis and is parallel to a floor surface on the basis of control signals from the central control device 200. The bed 101 moves the top plate at a bed movement speed and in a bed movement direction determined by the central control device 200 during scanning.

The gantry driving device 107 circumferentially rotates a potation, board of the gantry 100 on the basis of a control signal from the central control device 200.

The X-ray detection device 103 is formed by, for example, two-dimensionally arranging X-ray detection element groups each including a combination of a scintillator and a photodiode, in a channel direction (circumferential rotation direction) and a column direction (body axis direction). The X-ray detection device 103 is disposed to oppose the X-ray generation device 102 with the object 3 interposed therebetween. The X-ray detection device 103 detects a dose of X-rays which are irradiated from the X-ray generation device 102 and are transmitted through the object, and outputs the dose thereto to the data collecting device 106.

The data collecting device 106 collects information regarding X-ray dose detected by each X-ray detection element of the X-ray detection device 103, converts the information into a digital signal, and sequentially outputs the digital signal to the arithmetic device 202 of the operation unit 20 as transmitted X-ray information.

The arithmetic device 202 includes a reconstruction processing device 221, an image processing device 222, and the like.

The reconstruction processing device 221 acquires the transmitted X-ray information collected by the data collecting device 106, and creates projection data which is required to reconstruct an image. The reconstruction processing device 221 reconstructs a tomographic image (CT image) of the object 3 by using the projection data.

In the present invention, the reconstruction processing device 221 performs a successive approximation image reconstruction process which will be described later.

Consequently, a CT image in which noise is reduced is reconstructed at a high speed. Details of the successive approximation image reconstruction process performed by the arithmetic device 202 (reconstruction processing device 221) of the present invention will be described later. The reconstruction processing device 221 preserves the generated CT image in the storage device 213 and also displays the CT image on the display device 211.

The image processing device 222 performs image processing on the CT image which is created by the reconstruction processing device 221 and is stored in the storage device 213. An image having undergone the image processing is displayed on the display device 211 and is also preserved in the storage device 213.

Figure 3:
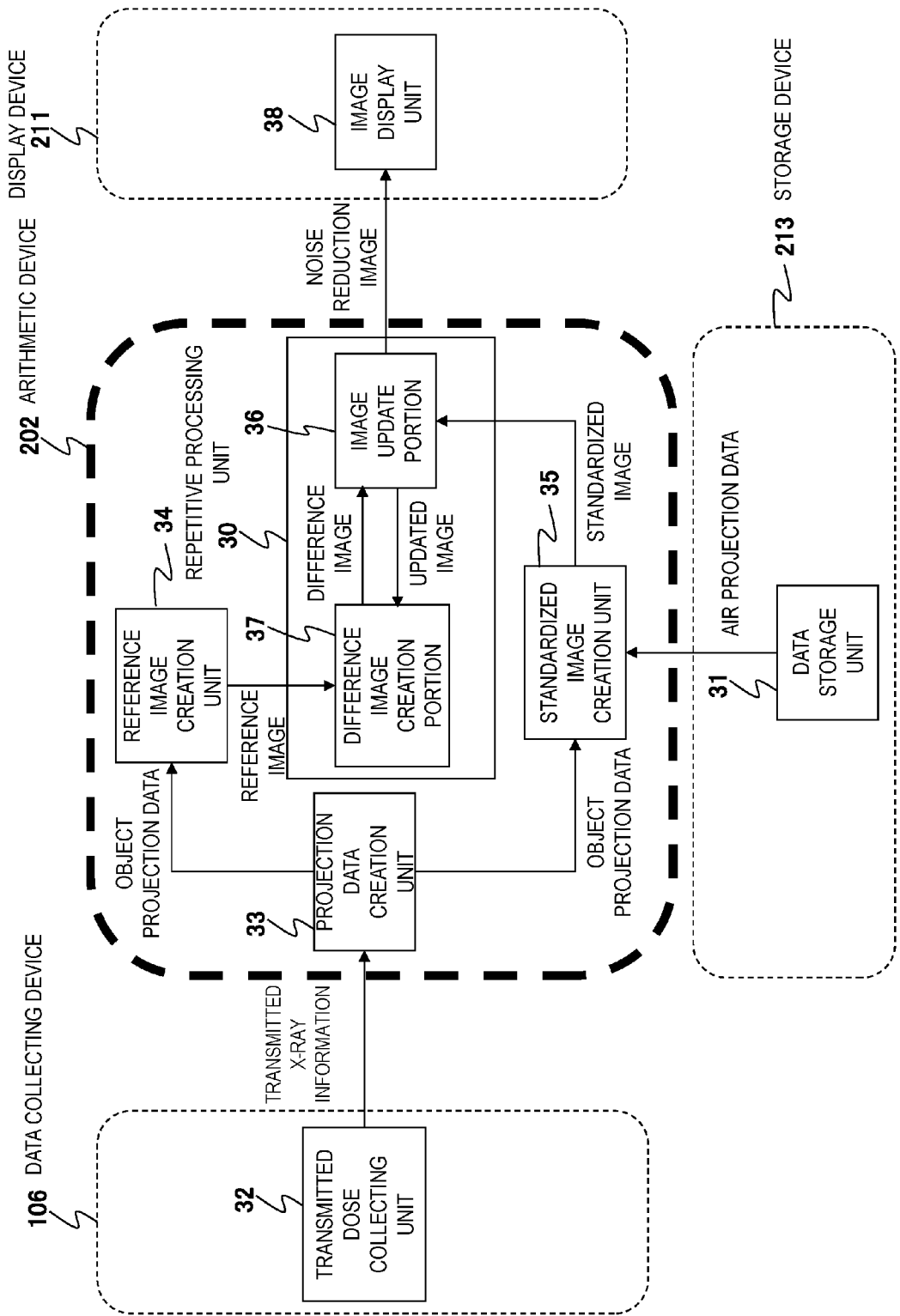
FIG. 3 is a functional block diagram of an arithmetic device 202.

Next, with reference to FIG. 3, a functional configuration of the X-ray CT apparatus 1 of the present invention will be described.

The X-ray CT apparatus 1 includes, as a functional configuration, a data storage unit 31, a transmitted dose collecting unit 32, a projection data creation unit 33, a reference image creation unit 34, a standardized image creation unit 35, a repetitive processing unit 30, and an image display unit 38. The repetitive processing unit 30 includes an image update portion 36 and a difference image creation portion 37.

The data storage unit 31 is a region storing air projection data which is measured in advance or is obtained through computation, and is provided in, for example, the storage device 213 of the operation unit 20. The data storage unit 31 transmits the air projection data to the standardized image creation unit 35. The air projection data is projection data which is measured through scanning in a state in which there are no object 3 and bed 101.

The transmitted dose collecting unit 32 collects transmitted X-ray information which is dose information of X-rays which are irradiated to the object 3 from the X-ray generation device 102 and are detected by the X-ray detection device 103 after being transmitted through the object 3 and the bed 101. The transmitted dose collecting unit 32 transmits the collected transmitted X-ray information to the projection data creation unit 33.

The projection data creation unit 33 acquires the transmitted X-ray information transmitted from the transmitted dose collecting unit 32, performs logarithmic conversion by multiplying the transmitted X-ray information by a predetermined logarithmic conversion coefficient, and thus creates object projection data which is required to reconstruct an image. The created object projection data is transmitted to the reference image creation unit 34 and the standardized image creation unit 35.

The reference image creation unit 34 reconstructs an object tomographic image by using the acquired object projection data, and uses the object tomographic image as a reference image in an image update process which will be described later. The reconstructed reference image is transmitted to the difference image creation portion 37. In the successive approximation image reconstruction process of the present invention, the reference image is initially referred to in the image update process which is repeatedly performed, and is also referred to every time.

The standardized image creation, unit 35 creates a standardized image in which a standardization coefficient for adjusting the noise reduction intensity in the image update process is defined for each pixel. Regarding specific creation procedures of the standardized image, for example, the standardized image creation unit 35 acquires and adds air projection data and object projection data together, takes an exponent by multiplying a result thereof by an inverse logarithmic conversion coefficient, and creates dose conversion projection data. An image which is reconstructed by using the dose conversion projection data is used as a standardized image.

The standardized image creation unit 35 transmits the created standardized image to the image update portion 36. A standardized image is not limited to an image reconstructed by using dose conversion projection data. For example, an image in which a CT value of an object tomographic image is non-negative may be used, and an image in which each pixel of an object tomographic image is converted by using a standardization coefficient corresponding to a CT value may be used.

The difference image creation portion 37 acquires an updated image from the image update portion 36, and takes a difference between a reference image and the updated image so as to create a difference image. The created difference image is sent to the image update portion 36.

The image update portion 36 performs an image update process by using an update formula (Equation (4) which will be described later) based on a successive approximation method by using the difference image acquired from the difference image creation portion 37 and the standardized image acquired from the standardized image creation unit 35.

The repetitive processing unit 30 performs a repetitive process a predetermined number of times by using the reference image created by the reference image creation unit 34 and the standardized image created by the standardized image creation unit 35. The repetitive process is a process in which creation of a difference image in the difference image creation portion 37 and creation of an updated image in the image update portion 36 are repeatedly performed a predetermined number of times of update. In a case where the predetermined number of times of update is not reached, the image update portion 36 transmits an updated image to the difference image creation portion 37, and creation of a difference image and the above-described image update process are repeatedly performed the predetermined number of times of update. In a case where the predetermined number of update is reached, image update is stopped. The image update portion 36 transmits an image obtained through the update process to the image display unit 38 as a noise reduction image.

The image display unit 38 displays the noise reduction image which is an image updated by the image update portion 36 on the display device 211.

The successive approximation image reconstruction process of the present invention is different from the successive approximation image reconstruction process (SPS method) of the related art in that the difference image creation portion 37 talking a difference between a reference image and an updated image is provided. In the related art, updated images are forward-projected whenever images are repeatedly updated, a difference between forward projection data and original object projection data is back-projected, and thus a difference image is obtained. In other words, the forward projection process and the back projection process are repeatedly performed. However, in the present invention, the forward projection process and the back projection process requiring calculation time are replaced with a process requiring a relatively small calculation amount, that is, a process of obtaining a difference between an updated image and a reference image. Thus, processing time for creating a difference image is considerably reduced.

Figure 4:
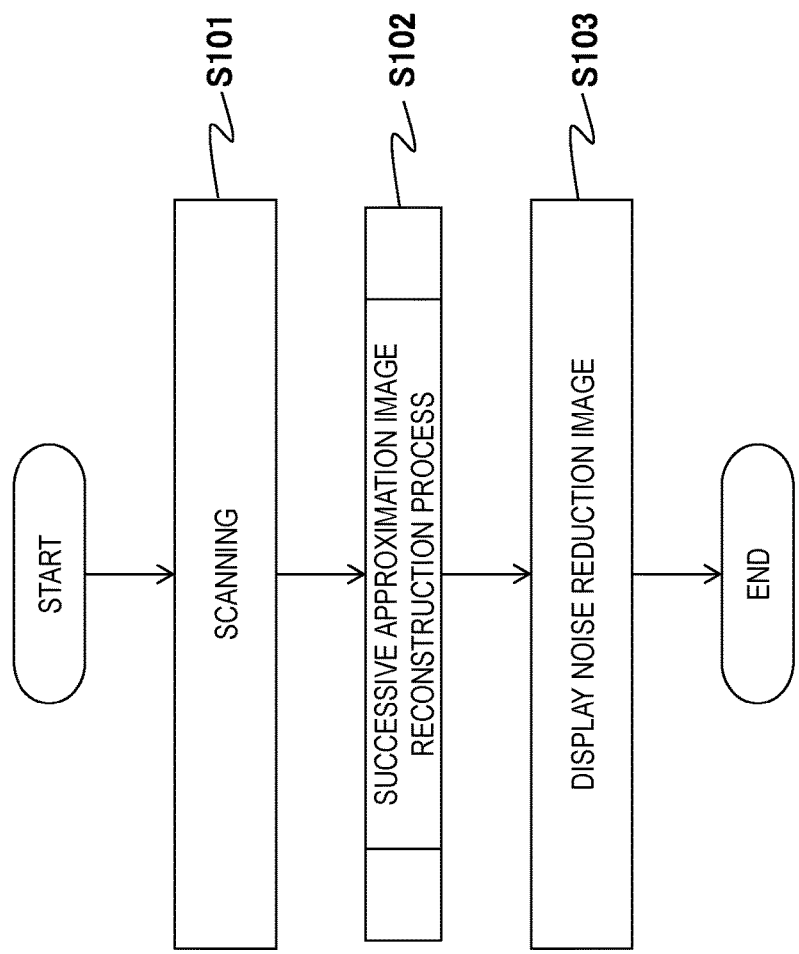
FIG. 4 is a flowchart illustrating a flow of the entire process.

Next, with reference to FIG. 4, a description will be made of a flow of the entire process in the X-ray CT apparatus 1 of the present invention.

First, the X-ray CT apparatus 1 performs positioning scanning on the object 3. In the positioning scanning, an irradiation direction of X-rays is fixed without rotating the gantry 100, and a dose of the X-rays having been transmitted through the object 3 and the bed 101 is measured while moving the bed 101 at a predetermined speed. The X-ray CT apparatus 1 creates a positioning image on the basis of transmitted X-ray data obtained through the positioning scanning.

The central control device 200 receives various set condition such as scanning conditions or reconstruction conditions by using the positioning image. The central control device 200 performs main scanning on the basis of the various set conditions. In the main scanning, X-rays are irradiated from respective directions around the object 3 by rotating the gantry 100, and X-ray information having been transmitted through the object 3 and the bed 101 is measured. Object projection data is acquired through this main scanning (step S101).

The arithmetic device 202 performs a successive approximation image reconstruction process by using the acquired object projection data (step S102). Details of the successive approximation image reconstruction process will be described later.

The arithmetic device 202 displays a noise reduction image created through the successive approximation image reconstruction process in step S102, on the display device 211 (step S103).

Next, with reference to FIG. 5, procedures of the successive approximation image reconstruction process in the above step S102 will be described.

Figure 5:
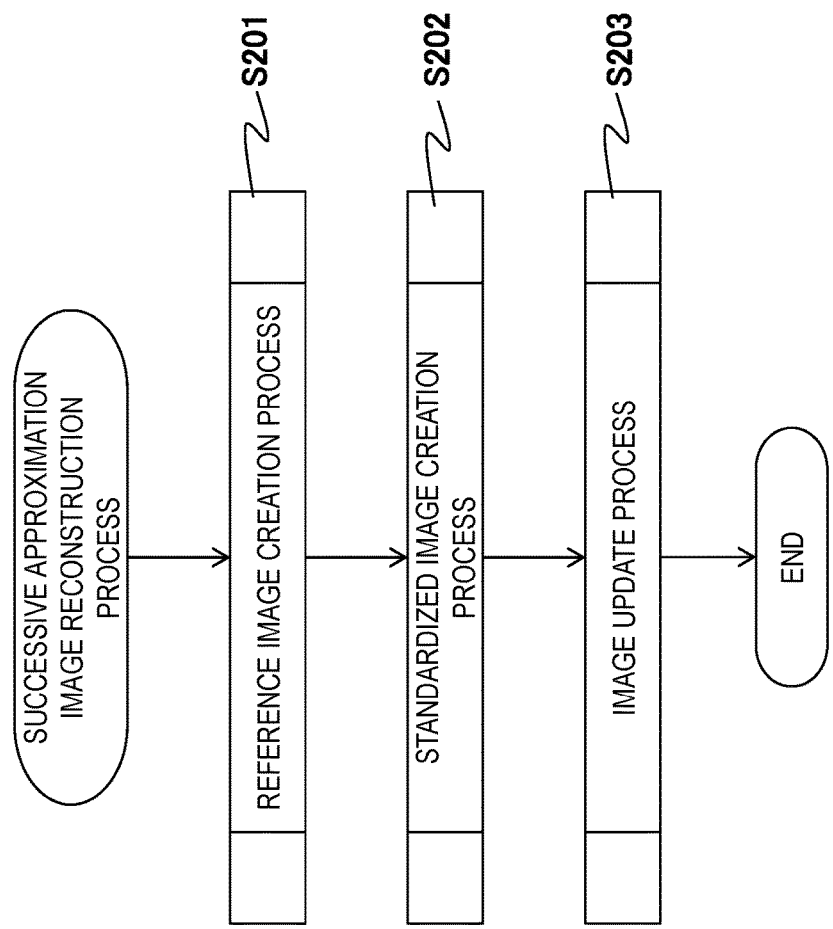
FIG. 5 is a flowchart illustrating a flow of a successive approximation image reconstruction process in step S102 in FIG. 4.

As illustrated in FIG. 5, the reconstruction processing device 221 of the arithmetic device 202 reconstructs an object tomographic image as a reference image in an image update process by using the object projection data obtained through the main scanning in step S101 (step S201). The created object tomographic image (reference image) is held in a RAM or the like, and is used in an image update process in step S203. A method of creating at reference image will be described later (refer to FIG. 6 and the like).

Next, the reconstruction processing device 221 creates a standardized image (step S202). Specifically, the reconstruction processing device 221 converts the object projection data acquired in step S101 into a dose conversion projection data by using air protection data stored in the storage device 213. The reconstruction processing device 221 sets an image reconstructed by using the dose conversion projection data, as a standardized image. The air projection data may be created in advance on the basis of transmitted X-ray information collected in a state in which an object and the bed 101 are not present in the gantry 100, and may be created through computation by taking into consideration a geometric system of the gantry 100. As described above, the dose conversion projection data is obtained by adding the air projection data and the object projection data together, multiplying a result thereof by an inverse logarithmic conversion coefficient, and taking an exponent.

The reconstruction processing device 221 repeatedly updates images by using the reference image created in step S201 and the standardized image created in step S202 (step S203). In step S203, calculation expressed in Equation (4) which will be described later is repeatedly performed a predetermined number of times (repetitive process).

In other words, images are repeatedly updated a predetermined number of times by using an update formula (Equation (4)) not including a back projection process and a forward projection process. Details of the image update process will be described later.

The back projection process and the forward projection process requiring a lot of processing time can be omitted and be replaced with an image difference process (a difference process between a reference image and an updated image) due to the processes in step S201 to step S203, and an image can be updated. Consequently, it is possible to obtain an updated image (noise reduction image) in which noise is reduced while reducing processing time.

The above-described process procedures are procedures of an image reconstruction process of the present invention. In the respective embodiments, specific aspects of a reference image or a standardized image will be described.

First Embodiment

Figure 6:
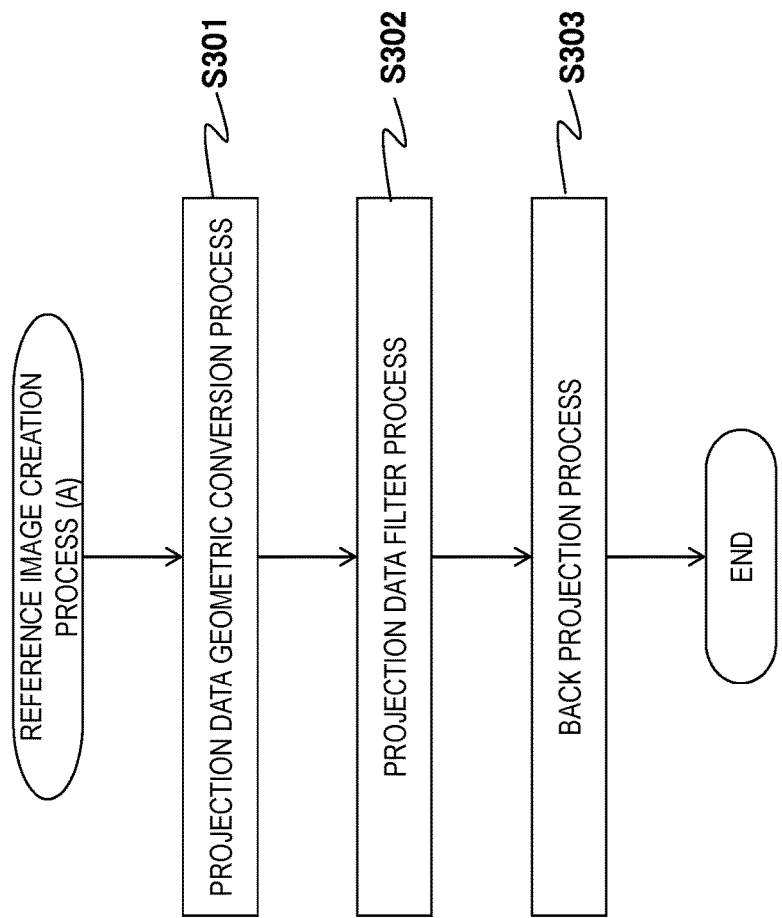
FIG. 6 is a flowchart illustrating a flow of a reference image creation process (A).
Figure 7:
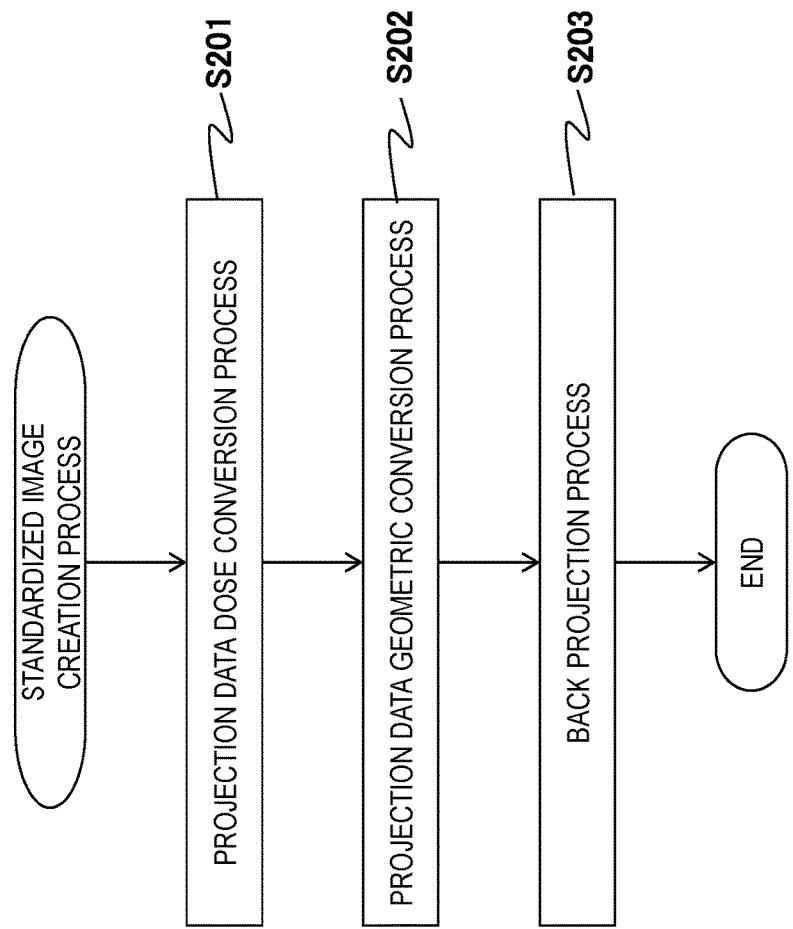
FIG. 7 is a flowchart illustrating a flow of a standardized image creation process.

With reference to FIGS. 6 and 7, a first embodiment of the present invention will be described in detail.

The X-ray CT apparatus 1 according to the first embodiment of the present invention is characterized in terms of normally using the same image without updating a reference image in an image update process. For example, an image reconstructed according to a filtered back projection method is used as a reference image.

FIG. 6 is a flowchart illustrating procedures of a reference image creation process (A) in a case where a reference image is created according to the filtered back projection method.

The X-ray CT apparatus 1 irradiates the object 3 with fan-shaped X-rays (fan beams) from the X-ray generation device 102 so as to collect transmitted X-ray information, and creates object projection data. The projection data obtained by irradiating fan-shaped X-rays will be referred to as fan-shaped irradiation projection data in the following description. When a reference image is created, first, the reconstruction processing device 221 performs a projection data geometric conversion process of converting the fan-shaped irradiation projection data into parallel irradiation projection data (step S301).

In the projection data geometric conversion process, pieces of fan-shaped irradiation projection data from a plurality of angles (views) are used and are converted into parallel irradiation projection data. The parallel irradiation projection data is projection data obtained in a case where X-rays are assumed to be irradiated to the object 3 in parallel. Through the process in step S301, it is possible to reduce a calculation amount in coordinate computation in a back projection process (step S303) which will be described later.

Next, the reconstruction processing device 221 performs a filtering process on the parallel irradiation projection data (step S302). In the filtering process, first, the reconstruction processing .device 221 performs Fourier transform on the parallel irradiation projection data, and multiplies an obtained frequency-domain parallel irradiation projection data by a frequency filter. Inverse Fourier transform is further performed, and thus filter parallel irradiation projection data is created.

The Fourier transform and the inverse Fourier transform may respectively employ a fast Fourier transform process (FFT) and an inverse fast Fourier transform process (IFFT). Consequently, a filtering process on projection data can be performed at a high speed. As the above-described frequency filter, for example, a normalization ramp filter is preferably used, but is only an example, and other filters may be used.

The reconstruction processing device 221 performs a back projection process on the filter parallel irradiation projection data obtained in step S302 (step S303). In other words, the reconstruction processing device 221 calculates a coordinate of a detection element located an intersection between a straight line passing through a focal point of the X-ray generation device 102 and the center of a target pixel and the X-ray detection device 103 for each rotation angle (view) of the scanner 10, and adds protection value of filter parallel irradiation, projection data. Corresponding to the calculated detection element position to the target pixel. If the same process is repeatedly performed on all pixels, an object tomographic image is created. The object tomographic image is set as a reference image used in the successive approximation image reconstruction process.

FIG. 7 is a flowchart illustrating detailed procedures of the standardized image creation process in step S202 in FIG. 5.

As illustrated in FIG. 7, first, the reconstruction processing device 221 performs a projection data dose conversion process (step S401). The projection data dose conversion process is a process of converting the object projection data which is data having undergone logarithmic conversion into data (dose conversion projection data) not having undergone logarithmic conversion.

As specific process procedures, the reconstruction processing device 221 adds fan-shaped irradiation projection data (object projection data) obtained from the data collecting device 106 to the air projection data acquired from the storage device 213, and acquires an exponent by multiplying an addition result by a predetermined conversion coefficient. Consequently, the object projection data is converted into fan-shaped irradiation dose conversion projection data. The fan-shaped irradiation dose conversion projection data is data which is obtained with fan beams and indicates a dose of X-rays having been transmitted through the object 3.

Next, the reconstruction processing device 221 performs the same process as the projection data geometric conversion process in step S301 on the fan-shaped irradiation dose conversion data obtained in step S401, so as to convert the fan-shaped irradiation dose conversion data into parallel irradiation dose conversion projection data (step S402).

The reconstruction processing device 221 performs the same process as the back projection process in step S303 by using the parallel irradiation dose conversion projection data obtained in step S402 instead of the filter parallel irradiation dose projection data. Consequently, a standardized image is obtained (step S403).

In the first embodiment, the reconstruction processing device 221 performs an image update process (step S203 in FIG. 5) by using the reference image created through the process procedures (filtered back projection method) in FIG. 6 and the standardized image created through the process procedures in FIG. 7.

Hereinafter, the update process will be described in detail.

In a general successive approximation reconstruction process (SPS method), image update is performed by using Equation (1).

On the other hand, in the first embodiment of the present invention, approximation shown in the following Expression (2) is used.

$$d_j \approx \sum \gamma_{ij} \sum a_{ik} \atop y_i \approx \sum a_{ik} \mu_k^{(0)}\Biggr\} \quad (2)$$

In other words, the reconstruction processing device 221 replaces the matrix calculation portion included in the update formula in Equation (1) with image difference calculation by using approximation shown in the following Expression (3).

$$\Sigma \gamma_{ij}(y_j - \Sigma a_{ik}\mu_k^{(n)}) \rightarrow d_j(\mu_j^{(0)} - \mu_j^{(n)}) \quad (3)$$

Consequently, an update formula becomes the following Equation (4).

$$\mu_j^{(n+1)} = \mu_j^{(n)} - \frac{d_j(\mu_j^{(0)} - \mu_j^{(n)}) + \beta \sum w_{jk} \phi(\mu_j^{(n)} - \mu_k^{(n)})}{d_j + 2\beta \sum w_{jk} \omega_\psi(\mu_j^{(n)} - \mu_k^{(n)})} \quad (4)$$

Here, $\mu_j^{(0)}$ indicates a reference image.

The reconstruction processing device 221 performs an image update process by using the Equation (4) which is an update formula from which the matrix calculation portion is removed.

As described above, the successive approximation image reconstruction process (SPS method) of the related art includes calculation of performing a back projection process on difference projection data between forward projection data created through a forward projection process on an updated image,, and object projection data, but, in the present invention, at reference image is used as a result, of a forward projection process on object projection data (approximation in Expression (2) is used). Consequently, the forward projection process and the back projection process which are matrix calculation causing a large calculation load can be omitted and be replaced with image processing (a difference between a reference image and an updated image) causing a small calculation load, and thus an update formula can be configured. As a result, a calculation amount in the successive approximation image reconstruction process can be considerably reduced, and thus processing time can be reduced.

Second Embodiment

Next, with reference to FIG. 8, a second embodiment of the present invention will be described.

The second embodiment is different from the first embodiment in that an image created by using projection data which is corrected through a successive approximation projection data correction process is used as a reference image in an image update process.

Figure 8:
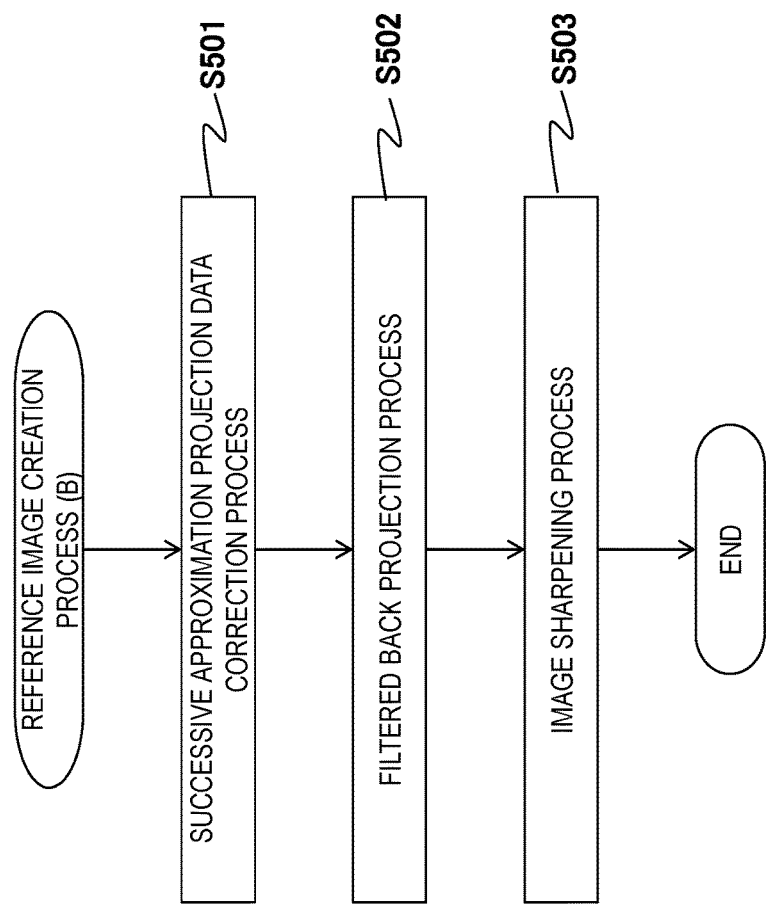
FIG. 8 is a flowchart illustrating a flow of a reference image, creation process (B).

With reference to FIG. 8, a description will be made of a reference image creation process (B) in the second embodiment.

The reconstruction processing device 221 acquires object projection data, and performs a successive approximation projection data correction process on the object projection data (step S501). In the successive approximation projection data correction process, the reconstruction processing device 221 repeatedly applies a convolution filter to the object projection data a predetermined number of times. A weighted average filter or the like having a smoothing effect is used for the integral kernel of the convolution filter.

Next, the reconstruction processing device 221 reconstructs an image by performing a filtered back projection process by using projection data (corrected object projection data) corrected through the successive approximation projection data correction process in step S501 (step S502). The filtered back projection process is the same as in the. reference image creation process (A) in the first embodiment. In other words, the reconstruction processing device 221 obtains an object tomographic image by performing a projection data geometric conversion process, a projection data filtering process, and a back projection process on the corrected object projection data. The object tomographic image is set as a first corrected tomographic image.

Next, the reconstruction processing device 221 applies a sharpening filter on the first corrected tomographic image obtained through the process in step S502, and sets a sharpened object tomographic image as a second corrected tomographic image (step S503). By applying the sharpening filter, a pixel value of a pixel which is excessively smoothed in the successive approximation projection data correction process is recovered. As the sharpening filter, a weighted average filter or the like formed of, for example, a Laplacian filter may be used.

The reconstruction processing device 221 uses the second corrected tomographic image created through the reference image creation process (B) in FIG. 8 as a reference image in the successive approximation image reconstruction process illustrated in FIG. 5. As a standardized image, an image created through the same process as the process in the first embodiment (refer to FIG. 7) may be used.

The reconstruction processing device 221 performs an image update, process according to the update formula expressed in Equation (4) by using the above-described second corrected tomographic image and the standardized image. Image update is repeatedly performed a predetermined number of times, and thus a noise reduction image is created.

As described above, in the second embodiment, a tomographic image (second corrected tomographic image) having undergone the successive approximation projection data correction process is used as a reference image as a result of performing a forward projection process on object projection data in the successive approximation image reconstruction process (SPS method) of the related art. Consequently, it is possible to provide a noise reduction image in which image quality is improved by reducing a streak artifact in addition to the effect of the first embodiment.

Third Embodiment

Next, with reference to FIG. 9, a third embodiment will be described in detail.

In the third embodiment, the X-ray CT apparatus 1 performs an image enlargement process before an image is updated in the update process (step S203 in FIG. 5) in the successive approximation image reconstruction process, and performs an image reduction process after the image is updated. As a reference image and a standardized image, images created according to the same method as that in the first or second embodiment may be used.

Figure 9:
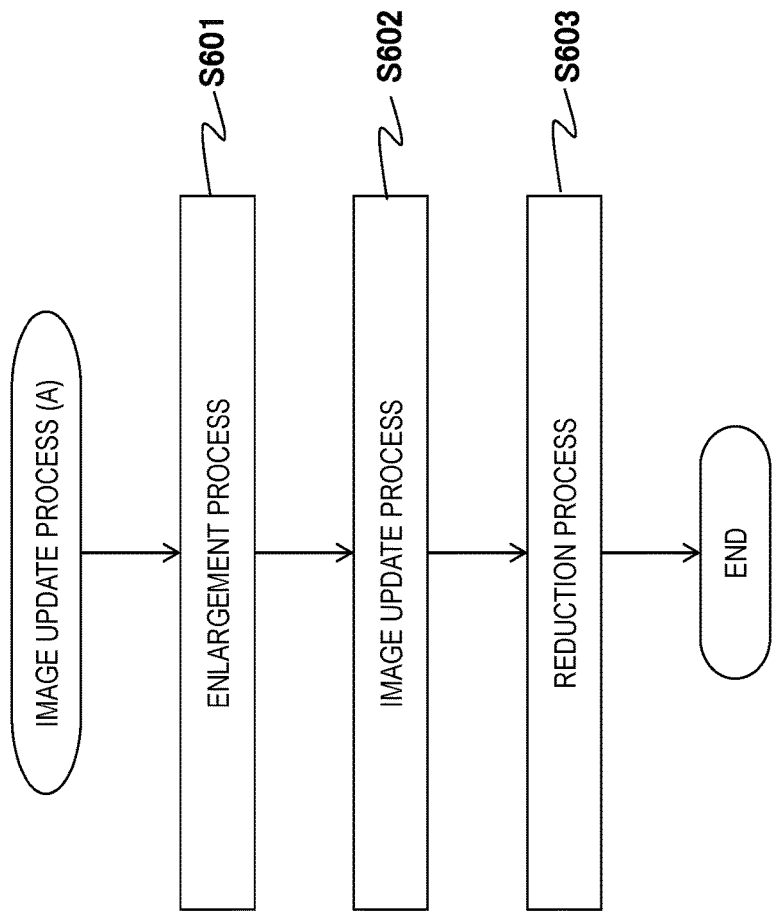
FIG. 9 is a flowchart illustrating a flow of an image update process (A).

FIG. 9 illustrates procedures of an image update process (A) in the third embodiment.

First, the reconstruction processing device 221 performs an image enlargement process (step S601).

In this enlargement process, the reconstruction processing device 221 creates an enlarged reference image obtained by increasing a size of a reference image in a section (axial plane) which is perpendicular to the bed 101 and is parallel to the gantry 100. For example, if an image size is increased to twice, a pixel size becomes a half of that of an original image. The reconstruction processing device 221 creates an enlarged standardized image by increasing a size of a standardized image in the same manner.

Next, the reconstruction processing device 221 repeatedly performs an update process based on Equation (4) in the same manner as in the first embodiment by using the enlarged reference image and the enlarged standardized image. Consequently, an enlarged noise reduction image is created (step S602).

The reconstruction processing device 221 reduces .a size of the enlarged noise reduction image in the axial plane, so as to obtain the same image size as that of the original reference image (step S603).

As described above, in the third embodiment, an update process is performed by using an enlarged image, and thus it is possible to maintain a shape of a small object in a noise reduction image in addition to the effect of the first embodiment. Consequently, it is possible to create a noise reduction image in which image quality is improved.

Fourth Embodiment

Next, a fourth embodiment of the present invention will be described.

In a successive approximation image reconstruction process of the fourth embodiment, a combined image is used as the reference image $\mu_j^{(0)}$ of the update formula (4). The combined image is an image obtained by combining a reference image (hereinafter, referred to as a first reference image) created according to the method (filtered back projection process) of the first embodiment with an updated image at a predetermined ratio.

First, the reconstruction processing device 221 creates a reference image and a standardized image in the same manner as in the first embodiment.

In the update process of step S203 in FIG. 5, the reconstruction processing device 221 replaces the reference image $\mu_j^{(0)}$ of the update formula expressed in Equation (4) with a combined image as in the following Expression (5).

$$\mu_j^{(0)} \rightarrow v_j^{(n)} \mu_j^{(0)} + (1 - v_j^{(n)}) \mu_j^{(n-1)} \quad (5)$$

Here, $v_j^{(0)}$ is a combination coefficient (weight) for pixel number j during n-th update. The combination coefficient may be any value designated previously by an operator, and may be determined on the basis of scanning conditions. As an updated image combined with the reference image, the previous updated image is used.

As mentioned above, in the successive approximation image reconstruction process according to the fourth embodiment, the reference image $\mu_j^{(0)}$ of the update formula (4) is replaced with a combined image obtained by multiplying a reference image and an updated image by a predetermined combination coefficient, and an update process is performed. Consequently, a difference, image "$\mu_j^{(0)} - \mu_j^{(n)}$" the update formula (4) can be prevented from being increased.

Through the process in the fourth embodiment, it is possible to increase a noise reduction effect and thus to provide a noise reduction image in which image quality is improved, in addition to the effect of the first embodiment.

Fifth Embodiment

Next, with reference to FIG. 10, a fifth embodiment will be described in detail.

In a successive approximation image reconstruction process according to the fifth embodiment, a standardized image in which noise is reduced is used as a standardized image.

The reconstruction processing device 221 creates a reference image and a standardized image in the same manner as in the first or second embodiment.

Figure 10:
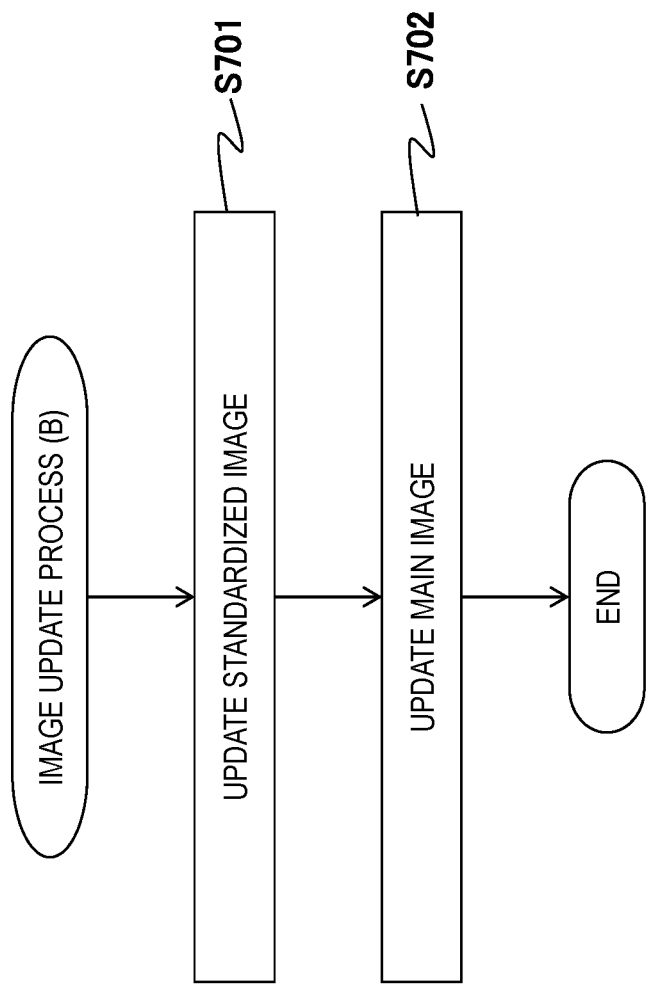
FIG. 10 is a flowchart illustrating a flow of an image update process (B).

In an image update process, the reconstruction processing device 221 performs an image update process (B) according to the procedures illustrated in FIG. 10.

In other words, the reconstruction processing device 221 updates the standardized image created according to, for example, the procedures illustrated in FIG. 7 a predetermined number of times as expressed in the following Equation. (6) (step S701). As a result of this process, a standardized image in which noise is reduced is obtained. Hereinafter, an image obtained through the process in step S701 will be referred to as a noise-reduced standardized image.

$$d_j^{(n+1)} = d_j^{(n)} - \frac{(d_j^0 - d_j^{(n)}) + \beta \sum w_{jk}\, \phi(d_j^{(n)} - d_k^{(n)})}{1 + 2\beta \sum w_{jk}\, \omega_{ij}(d_j^{(n)} - d_k^{(n)})} \quad (6)$$

Equation (6) is obtained by applying approximation based on the following Expression (7) to the above update formula (4).

$$\left. \begin{array}{l} \mu \to d \\ d \to 1 \end{array} \right\} \quad (7)$$

The reconstruction processing device 221 updates an image in the same manner as in the update process (Equation (4)) according to the first embodiment by using the reference image and the noise-reduced standardized image. Consequently, a noise reduction image is obtained.

As mentioned above, in the fifth embodiment, a standardized image in which noise is reduced is used as a standardized image, and noise is reduced by performing an update process on the standardized image. Consequently, it is possible to increase a noise reduction effect and thus to provide a noise reduction image in which image quality is improved, in addition to the effect of the first embodiment.

Sixth Embodiment

Next, with reference to FIGS. 11 and 12, a sixth embodiment will be described in detail.

In the sixth embodiment, in a successive approximation image reconstruction process, the X-ray CT apparatus 1 can set different standardization coefficients inside and outside a region of interest, designated by an operator on an object tomographic image. A standardized image is an image used to adjust the noise reduction intensity in an image for each pixel during image update, and thus the noise reduction intensity of a region of interest designated by an operator can be freely set through the operator's operation.

First, the reconstruction processing device 221 creates a reference image in the same manner as in the first or second embodiment.

In the sixth embodiment, designation of a region of interest from an operator is received in a standardized image creation process. Thus, the reconstruction processing device 221 displays the reference image on the display device 211.

Figure 11:
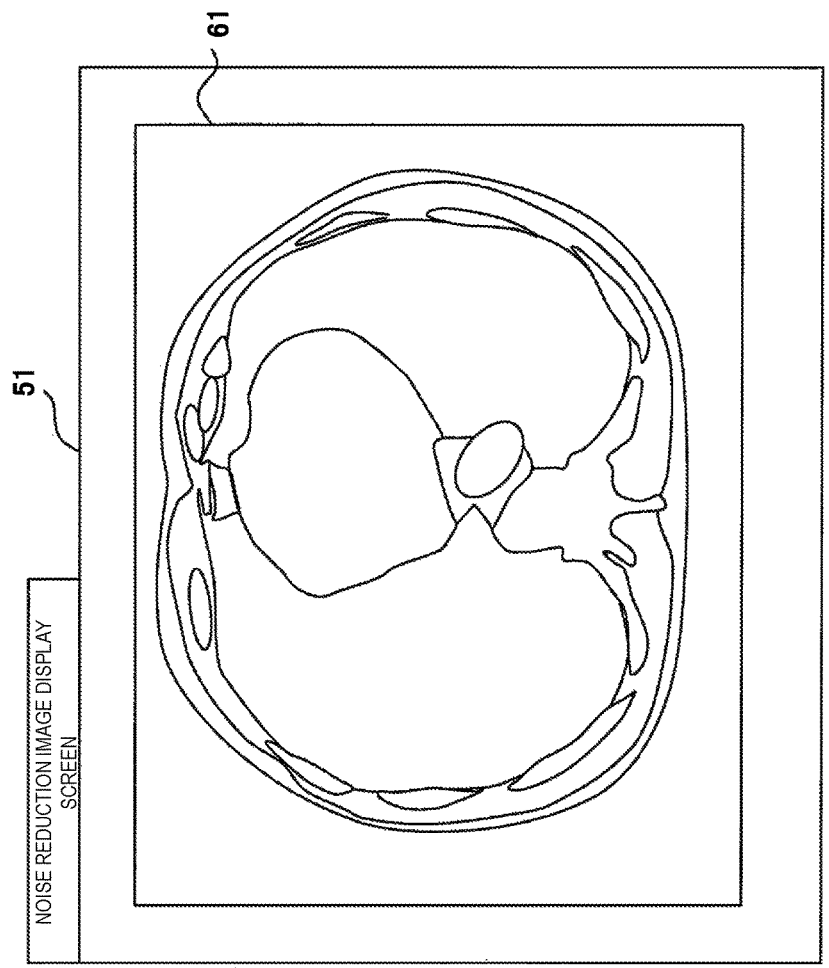
FIG. 11 illustrates an example of a noise reduction image display screen 51.

FIG. 11 illustrates an example of a display screen 51 for designating a region of interest. An object tomographic image (reference image) 61 is displayed on the display screen 51.

Figure 12:
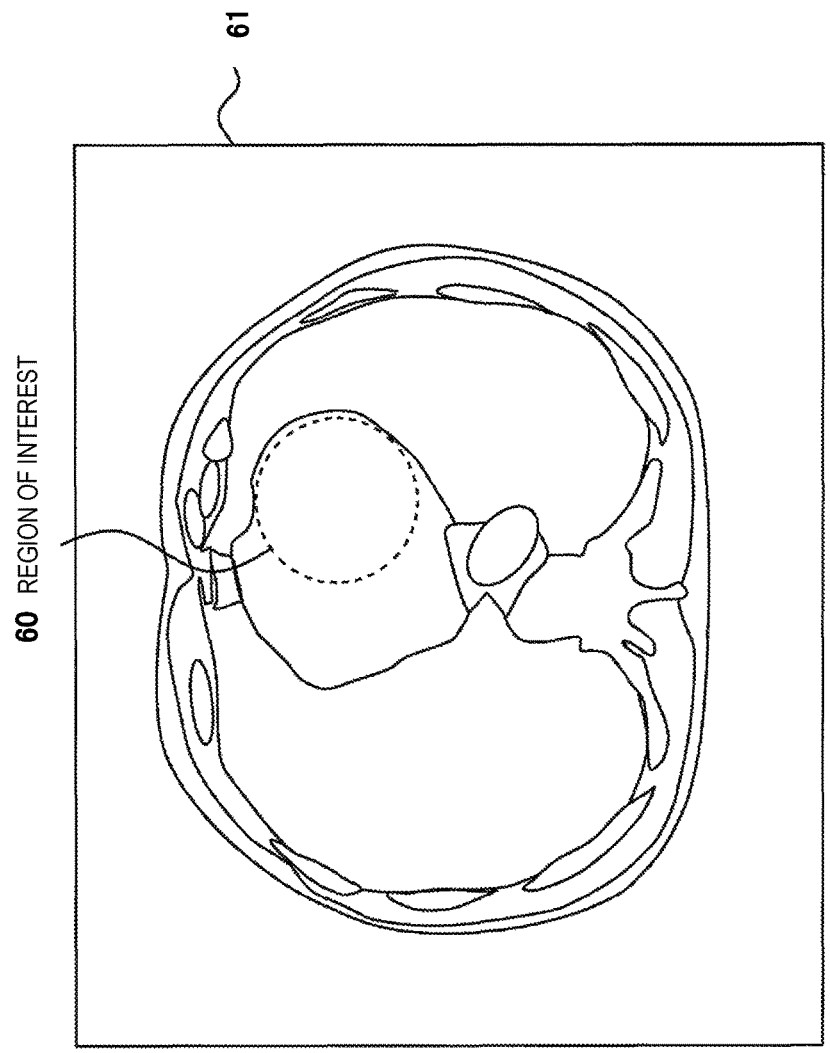
FIG. 12 illustrates an example of setting a region of interest 60 on a tomographic image.

The operator designates a region of interest 60 as illustrated in FIG. 12 on the displayed object tomographic image 61 as illustrated in FIG. 11 by using the input device 212 such as the mouse. The reconstruction processing device 221 sets a standardization coefficient of each pixel of the standardized image on the basis of coordinate information of a boundary between the inside and the outside of the region of interest 60 designated by the operator.

In this case, the reconstruction processing device 221 preferably sets the standardization coefficient of the inside of the region of interest 60 to be large, and sets the standardization coefficient of the outside of the region of interest 60 to be small. If the standardization coefficient is set to be large, the noise reduction intensity of the part can be increased. A standardization coefficient is preferably set to be smoothly continued with respect to the boundary between the inside and the outside of the region of interest 60. A standardization coefficient may be smoothly changed depending on a distance from the region of interest 60.

The number of region of interest 60 is not limited to one, and a plurality of regions of interest may be set.

As mentioned above, according to the sixth embodiment, different standardization coefficients can be set inside and outside a region of interest. Consequently, for example, the extent of noise reduction of a region of interest can be increased, and thus the noise reduction intensity can be freely set.

Seventh Embodiment

Next, a seventh embodiment will be described in detail.

In a successive approximation image reconstruction process of the seventh embodiment, a standardized image corresponding to tissue is used by taking into consideration that a CT value differs for each piece of tissue. An image obtained by performing at correction process on an object tomographic image according to the following procedures is used as a standardized image.

In the successive approximation image reconstruction process, first, the reconstruction processing device 221 creates a reference image (object tomographic image) in the same manner as in the first or second embodiment.

Next, the reconstruction processing device 221 creates a standardized linage. In the seventh embodiment, as described above, an image, obtained by performing a correction, process on an object tomographic image is used as a standardized image. Hereinafter, correction of an object tomographic image will be described.

A pixel value of an object tomographic image is a CT value, and may thus include a negative number. An image including a negative number is not suitable as a standardized image, and thus the reconstruction processing device 221 performs non-negative value processing on a pixel value of an object tomographic image so as to create a non-negative value image not including a negative number. In a case where the minimum value of a pixel value is a negative number, non-negative value processing may be performed by subtracting the minimum negative value from each pixel value. In the seventh embodiment, the non-negative value image is used as a standardized image. In a case where an object, tomographic image does not include a negative number, the object tomographic image may be used as a standardized image without any processing.

Another example of a correction process on an object tomographic image may include correction using a correlation function 80 in which a correlation between a CT value and a standardization coefficient is set.

In other words, the reconstruction processing device 221 converts each pixel of the object tomographic image to have a standardization coefficient corresponding to a pixel value by using a function (correlation function 80) indicating a correlation between a CT value and a standardization coefficient as illustrated in FIG. 13. An image in which a CT value is converted into a standardization coefficient as mentioned above is used as a standardized image in an update process.

Also in this case, the correlation function 80 which causes a standardization coefficient to be a non-negative value is used.

In this case, it is preferable to use the correlation function 80 which increases a standardization coefficient of a CT value corresponding to tissue in which a noise reduction effect is desired to be relatively increased. The example illustrated in FIG. 13 shows the correlation function 80 which increases a standardization coefficient of a CT value corresponding to soft tissue.

As described above, the reconstruction processing device 221 uses a non-negative value image obtained from an object tomographic image or an image obtained through conversion using the correlation function 80, as a standardized image in an image update process. The reconstruction processing device 221 may display the created standardized image on the display device 211 so as to present the standardized image to the operator.

An update process is performed in the same manner as in the first embodiment by using the reference image, and the reference image which is created as described above.

As described above, in the seventh embodiment, an image in which a standardization coefficient is set on the basis of CT value information of an object tomographic image is used as a standardized image. Thus, it is possible to further achieve a noise reduction effect corresponding to tissue in addition to the effect of the first embodiment. Consequently, it is possible to provide a noise reduction image in which image quality of tissue desired to be of interest by an operator is improved.

As mentioned above, preferred embodiments of the present invention have been described, but the present invention is not limited to the above-described embodiments. It is clear that a person skilled in the art can conceive of various modifications or alterations within the technical spirit disclosed in the present specification, and it is understood that they are naturally included in the technical scope of the present invention.

INDUSTRIAL APPLICABILITY

According to the present invention, it is possible to provide an arithmetic device, an X-ray CT apparatus, and an image reconstruction method, capable of reducing processing time while maintaining a noise reduction effect.

REFERENCE SIGNS LIST

1 X-RAY CT APPARATUS, 3 OBJECT, 10 SCANNER, 20 OPERATION UNIT, 100 GANTRY, 101 BED, 102 X-RAY GENERATION DEVICE, 103 X-RAY DETECTION DEVICE, 104 COLLIMATOR, 105 HIGH VOLTAGE GENERATION DEVICE, 106 DATA COLLECTING DEVICE, 107 GANTRY DRIVING DEVICE, 200 CENTRAL CONTROL DEVICE, 201 INPUT/OUTPUT DEVICE, 202 ARITHMETIC DEVICE, 211 DISPLAY DEVICE, 212 INPUT DEVICE, 213 STORAGE DEVICE, 221 RECONSTRUCTION PROCESSING DEVICE, 222 IMAGE PROCESSING DEVICE, 30 REPETITIVE PROCESSING UNIT, 31 DATA STORAGE UNIT, 32 TRANSMITTED DOSE COLLECTING UNIT, 33 PROJECTION DATA CREATION UNIT, 34 REFERENCE IMAGE CREATION UNIT, 35 STANDARDIZED IMAGE CREATION UNIT, 36 IMAGE UPDATE PORTION, 37 DIFFERENCE IMAGE CREATION PORTION, 38 IMAGE DISPLAY UNIT, 51 DISPLAY SCREEN, 60 REGION OF INTEREST, 61 REFERENCE IMAGE, 80 CORRELATION FUNCTION

The invention claimed is:

1. An arithmetic device comprising:
a projection data creation unit that creates object projection data on the basis of information regarding X-rays which are irradiated from respective directions around an object and are transmitted through the object;
a reference image creation unit that creates a reference image on the basis of the object projection data;
a standardized image creation unit that creates a standardized image in which a standardization coefficient for adjusting the noise reduction intensity in an update process is defined for each pixel; and
a repetitive processing unit that performs repetitive processes a predetermined number of times by using the reference image and the standardized image,
wherein the repetitive processing unit includes
a difference image creation portion that obtains a difference between the reference image and an updated image which is obtained through the update process, so as to create a difference image, and
an image update portion that performs the update process by using the difference image and the standardized image, so as to create an updated image.

2. The arithmetic device according to claim 1,
wherein the reference image creation unit creates a reference image according to a filtered back projection method.

3. The arithmetic device according to claim 1,
wherein the reference image creation unit performs a noise reduction process on the object projection data so as to create corrected projection data, creates a first corrected tomographic image by reconstructing an image by using the created corrected projection data, and creates a second corrected tomographic image in which a sharpening process is performed on the created first corrected tomographic image, as the reference image.

4. The arithmetic device according to claim 1,
wherein the repetitive processing unit repeatedly performs creation of the difference image and the update process a predetermined number of times by using an enlarged tomographic image and an enlarged standardized image obtained through enlargement, of sizes of images as a reference image in the difference image creation portion and a standardized image in the image update portion, so as to create an enlarged updated image, and creates a reduced image obtained by reducing the enlarged updated image to an original size.

5. The arithmetic device according to claim 1, wherein an image obtained by combining the reference image with the updated image at a predetermined ratio is used as a reference image in the difference image creation portion.

6. The arithmetic device according to claim wherein an updated standardized image is created by performing the update process by using a standardized image created by the standardized image creation unit as a reference image in the image update portion and the difference image creation portion, and the updated standardized image created is used as a standardized image in the image update portion.

7. The arithmetic device according to claim 1, further comprising:
a region of interest setting unit that sets a region of interest on the reference image; and
a setting unit that sets standardization coefficients which is different, from each other inside and outside the region of interest,
wherein the standardized image creation unit creates a standardized image in which the set standardization coefficient is defined for each pixel.

8. The arithmetic device according to claim 1, wherein the standardized image creation unit adds the object projection data to air projection data, takes an exponent by multiplying an addition result by an inverse logarithmic conversion coefficient, so as to obtain dose conversion data, and creates the standardized image by reconstructing an image by using the dose conversion data.

9. The arithmetic device according to claim 1, wherein the standardized image creation unit uses, as the standardized image, a non-negative value image in which a CT value of a tomographic image of the object is non-negative.

10. The arithmetic device according to claim 1, wherein the standardized image creation unit calculates a standardized image by using a tomographic image of the object on the basis of a correlation function in which a correlation between a CT value and a standardization coefficient is set.

11. An X-ray CT apparatus comprising the arithmetic device according to claim 1.

12. An image reconstruction method comprising:
causing an arithmetic device to execute:
a projection data creation step of creating object projection data on the basis of information regarding X-rays which are irradiated from respective directions around an object and are transmitted through the object.;
a reference image creation step of creating a reference image on the basis of the object projection data;
a standardized image creation step of creating a standardized image in which a standardization coefficient for adjusting the noise reduction intensity in an update process is defined for each pixel; and
a repetitive processing step of performing repetitive processes at predetermined number of times by using the reference image and the standardized image,
wherein the repetitive processing step includes
a difference image creation step of obtaining a difference between the reference image and an updated image which is obtained through the update process, so as to create a difference image, and
an image update step of performing the update process by using the difference image and the standardized image, so as to create an updated image.

* * * * *